US 12,419,641 B2

(12) United States Patent
Higdon et al.

(10) Patent No.: US 12,419,641 B2
(45) Date of Patent: Sep. 23, 2025

(54) APPARATUS FOR ANASTOMOSING A CUT VESSEL

(71) Applicant: Vanderbilt University, Nashville, TN (US)

(72) Inventors: Kent K. Higdon, Nashville, TN (US); Stephane A. Braun, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 340 days.

(21) Appl. No.: 18/004,495

(22) PCT Filed: Jun. 3, 2021

(86) PCT No.: PCT/US2021/035754
§ 371 (c)(1),
(2) Date: Jan. 6, 2023

(87) PCT Pub. No.: WO2022/010601
PCT Pub. Date: Jan. 13, 2022

(65) Prior Publication Data
US 2023/0240681 A1  Aug. 3, 2023

Related U.S. Application Data

(60) Provisional application No. 63/049,270, filed on Jul. 8, 2020.

(51) Int. Cl.
*A61B 17/11*   (2006.01)
(52) U.S. Cl.
CPC ....... *A61B 17/11* (2013.01); *A61B 2017/1107* (2013.01); *A61B 2017/1132* (2013.01)

(58) Field of Classification Search
CPC ............... A61B 17/11; A61B 17/115; A61B 2017/1107; A61B 2017/1132; A61B 2017/1135
See application file for complete search history.

(56) References Cited

U.S. PATENT DOCUMENTS

| 3,254,651 | A  |   | 6/1966 | Collito |
| 7,094,251 | B2 | * | 8/2006 | Bonutti ............ A61B 17/0487 606/232 |

(Continued)

OTHER PUBLICATIONS

International Search Report and Written Opinion dated Oct. 6, 2021 for corresponding International PCT Application No. PCT/US2021/035754.

*Primary Examiner* — Vi X Nguyen
(74) *Attorney, Agent, or Firm* — Tarolli, Sundheim, Covell &Tummino LLP

(57) ABSTRACT

An apparatus for anastomosing a cut vessel is provided. The apparatus includes a first ring having an inner surface that defines inner lumen. The inner lumen is configured to receive a first vessel end of the cut vessel. The inner surface of the first ring has at least one spike configured to penetrate the first vessel end and secure the first ring to the first vessel end. A second ring has an inner surface defining an inner lumen configured to receive a second vessel end of the cut vessel. The inner surface of the second ring has at least one spike configured to penetrate the second vessel end and secure the second ring to the second vessel end. The first and second rings, after being secured to the first and second vessel ends, are configured to be joined together into direct engagement to anastomose the cut vessel.

22 Claims, 8 Drawing Sheets

(56) References Cited

U.S. PATENT DOCUMENTS

| | | |
|---|---|---|
| 7,837,697 B2 | 11/2010 | Borghi |
| 7,922,734 B2 | 4/2011 | Blatter |
| 2005/0096699 A1* | 5/2005 | Wixey ............... A61B 17/0487 606/232 |
| 2012/0215238 A1* | 8/2012 | Borghi .................. A61B 17/11 606/153 |

* cited by examiner

APPARATUS FOR ANASTOMOSING A CUT VESSEL

RELATED APPLICATION DATA

This application is a U.S. National Stage under 35 USC 371 of PCT Application Serial No. PCT/US2021/036754, filed on 3 Jun. 2021, which claims priority from U.S. Provisional Application No. 63/049,270, filed 8 Jul. 2020, the subject matter of which is incorporated herein by reference in its entirety.

TECHNICAL FIELD

This disclosure relates to an apparatus and method for anastomosing a cut vessel.

BACKGROUND

Microsurgical vessel connections called anastomoses may be performed with either classic suture techniques—which can take thirty minutes per vessel or as long as two hours or more, due to complexity of multiple tiny microsutures being placed in the vessel—or, in the case of veins, with a vein coupler device. A vein coupler device may include two separate plastic rings. Each plastic ring has longitudinally extending metallic spikes. During a vein anastomosis, a medical professional rolls the edges of a cut end of a vein onto the spikes. Using a forceps, or another device, the edges of the cut end of the vein are tamped down onto the spikes. The plastic rings are then joined to a delivery device that compresses the spikes of one of the plastic rings into receiving holes on the other of the plastic rings.

Arteries can be much less distensible, less compliant, and thicker than veins. Arteries also have different vessel wall characteristics than veins. Therefore, vein coupler devices, being designed for coupling veins, may be inadequate when used for arterial anastomoses.

SUMMARY

In an aspect, an apparatus for anastomosing a cut vessel is provided. The apparatus comprises a first ring having longitudinally spaced first and second ring surfaces and an inner surface longitudinally extending between the first and second ring surfaces. The inner surface defines an inner lumen configured to receive a first vessel end of the cut vessel. The inner surface has at least one spike extending away from the inner surface into the inner lumen. The at least one spike of the first ring is configured to penetrate a vessel wall of the first vessel end and secure the first ring to the first vessel end. A second ring has longitudinally spaced first and second ring surfaces and an inner surface longitudinally extending between the first and second ring surfaces. The inner surface defines an inner lumen configured to receive a second vessel end of the cut vessel. The inner surface has at least one spike extending away from the inner surface into the inner lumen. The at least one spike of the second ring is configured to penetrate a vessel wall of the second vessel end and secure the second ring to the second vessel end. The first and second rings, after being secured to the first and second vessel ends, are configured to be joined together into direct engagement to anastomose the cut vessel.

In an aspect, alone or in combination with any other aspect, a method anastomosing a cut vessel is provided. The method comprises providing the apparatus. The first ring is positioned over a first vessel end of the cut vessel so that the first vessel end is in the inner lumen and surrounded by the inner surface of the first ring. A vessel wall of the first vessel end is penetrated with the at least one spike that extends away from the inner surface of the first ring to secure the first ring to the first vessel end. The second ring is positioned over a second vessel end of the cut vessel so that the second vessel end is in the inner lumen and surrounded by the inner surface of the second ring. A vessel wall of the second vessel end is penetrated with the at least one spike that extends away from the inner surface of the second ring to secure the second ring to the second vessel end. With the first and second rings secured to the first and second vessel ends, the first and second rings are joined together to anastomose the cut vessel.

In an aspect, alone or in combination with any other aspect, an apparatus for anastomosing a cut vessel is provided. The apparatus comprises a first ring having longitudinally spaced first and second ring surfaces and an inner surface longitudinally extending between the first and second ring surfaces. The inner surface defines an inner lumen configured to receive a first vessel end of the cut vessel. The first ring includes an annular central recession between the inner surface and the first ring surface. The annular recession is defined by a longitudinally extending recession sidewall and a laterally extending recession floor. The recession floor includes at least one spike longitudinally extending away from the recession floor. The at least one spike is configured to penetrate a vessel wall of the first vessel end. A second ring has longitudinally spaced first and second ring surfaces and an inner surface longitudinally extending between the first and second ring surfaces. The inner surface defines an inner lumen configured to receive a second vessel end of the cut vessel. The second ring includes an annular central recession between the inner surface and the first ring surface. The annular recession is defined by a longitudinally extending recession sidewall and a laterally extending recession floor. The recession floor includes at least one spike longitudinally extending away from the recession floor. The at least one spike is configured to penetrate a vessel wall of the second vessel end. The first and second rings, after being secured to the first and second vessel ends, are configured to be joined together to anastomose the cut vessel.

In an aspect, alone or in combination with any other aspect, a method anastomosing a cut vessel is provided. The method comprises providing the apparatus. The first ring is positioned over a first vessel end of the cut vessel so that the first vessel end is in the inner lumen and surrounded by the inner surface of the first ring. An edge of the first vessel end is everted onto the central recession of the first ring. The vessel wall of the first vessel end is penetrated with the at least one spike that extends away from the recession floor of the first ring to secure the first ring to the edge of the first vessel end. The second ring is positioned over a second vessel end of the cut vessel so that the second vessel end is in the inner lumen and surrounded by the inner surface of the second ring. An edge of the second vessel end is everted onto the central recession of the second ring. The vessel wall of the second vessel end is penetrated with the at least one spike that extends away from the recession floor of the second ring to secure the second ring to the edge of the second vessel end. With the first and second rings secured to the first and second vessel ends, the first and second rings are joined together to anastomose the cut vessel.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Figure 1:
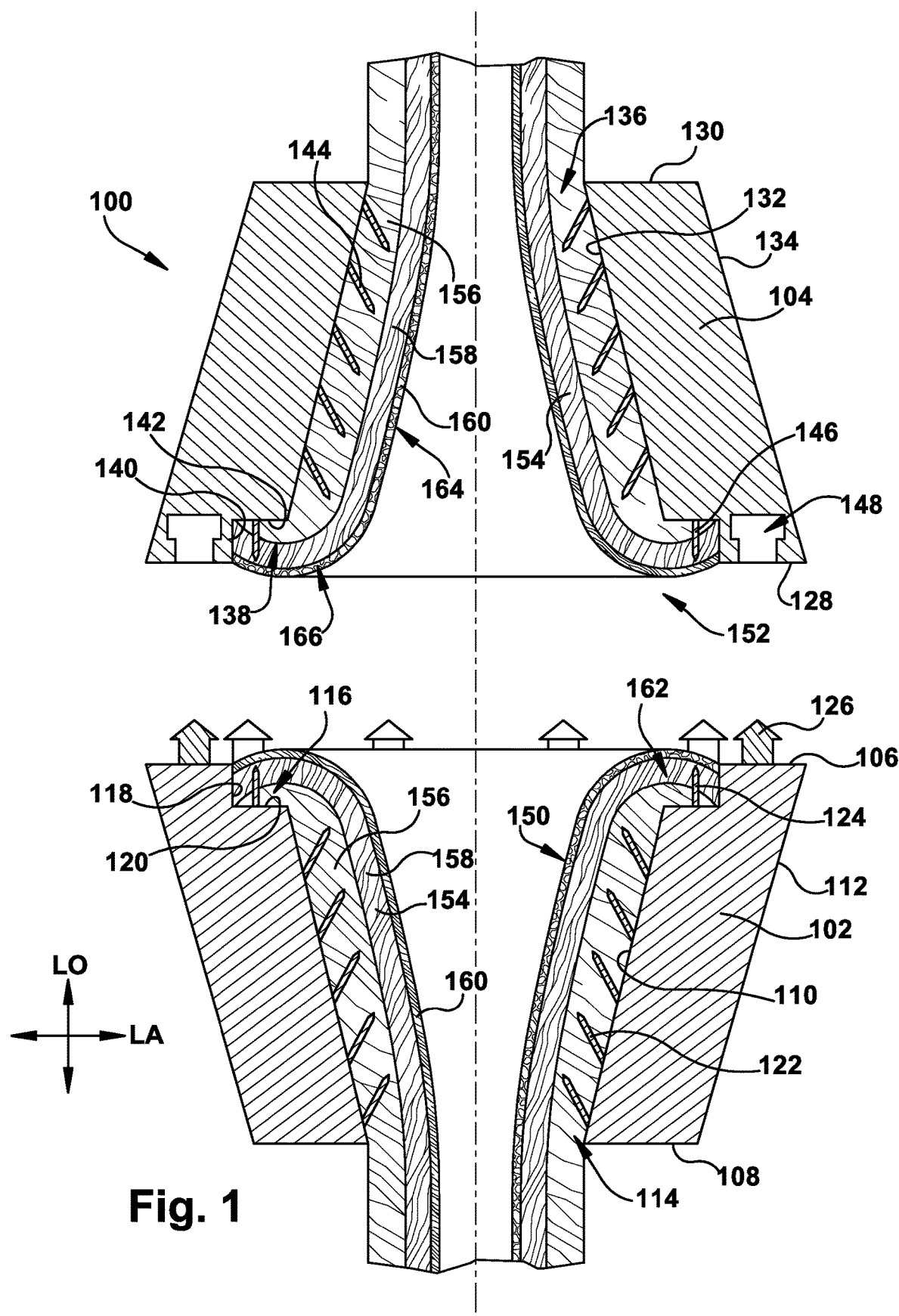
FIG. 1 is a cross-sectional view of an anastomotic coupler device according to an aspect of the present invention, including the device in an example use environment.

Unless defined otherwise, all technical and scientific terms used herein have the same meaning as is commonly understood by one of ordinary skill in the art to which the present disclosure pertains.

As used herein, the term "user" can be used interchangeably to refer to an individual who prepares for, assists with, and/or performs a procedure.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the phrase "at least one of X and Y" can be interpreted to include X, Y, or a combination of X and Y. For example, if an element is described as having at least one of X and Y, the element may, at a particular time, include X, Y, or a combination of X and Y, the selection of which could vary from time to time. In contrast, the phrase "at least one of X" can be interpreted to include one or more Xs.

It will be understood that when an element is referred to as being "on," "attached" to, "coupled" with, "contacting," etc., another element, it can be directly on, attached to, coupled with or contacting the other element or intervening elements may also be present. In contrast, when an element is referred to as being, for example, "directly contacting" another element, there are no intervening elements present.

Spatially relative terms, such as "over" and the like, may be used herein for ease of description to describe one element or feature's relationship to another element(s) or feature(s) as illustrated in the Figures. It will be understood that the spatially relative terms can encompass different orientations of a device in use or operation, in addition to the orientation depicted in the Figures. For example, if a device in the Figures is inverted, elements described as "over" other elements or features would then be oriented "under" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or Figures unless specifically indicated otherwise.

The invention comprises, consists of, or consists essentially of the following features, in any combination.

A device according to aspects of the present disclosure solves the problem of prior art anastomotic coupler devices, which may be inadequate when used for arterial anastomosis due to their design being based only upon on the characteristics of veins. The wall of an artery is not like a vein wall. Veins are thinner, more distensible, and more easily everted over an edge of an anastomotic coupler device than are arteries. Everting arteries and veins helps to achieve intima-to-intima coaptation during an anastomosis, which helps preclude the unwanted creation of a thrombosis (clotting failure of the vessel connection) during the anastomosis. A device according to the aspects of the prevent disclosure overcomes the issues of the prior art anastomotic coupler devices by being designed for arterial use.

The device disclosed herein also cuts down on the cost of an arterial anastomosis by reducing the time it takes to complete the anastomosis. Because prior art anastomotic coupler devices are inadequate when used for arterial anastomoses, medical professionals are left with using multiple tiny microsutures that can take 30-60 minutes per anastomosis on average and can take as long as 120 minutes or more in complex cases. Use of the device of the present disclosure for an arterial anastomosis may cut the average anastomosis time from 30-60 minutes down to around 5 minutes. Thus, the device of the present invention may reduce the cost of surgery by reducing operating room time for arterial anastomoses.

Figure 2:
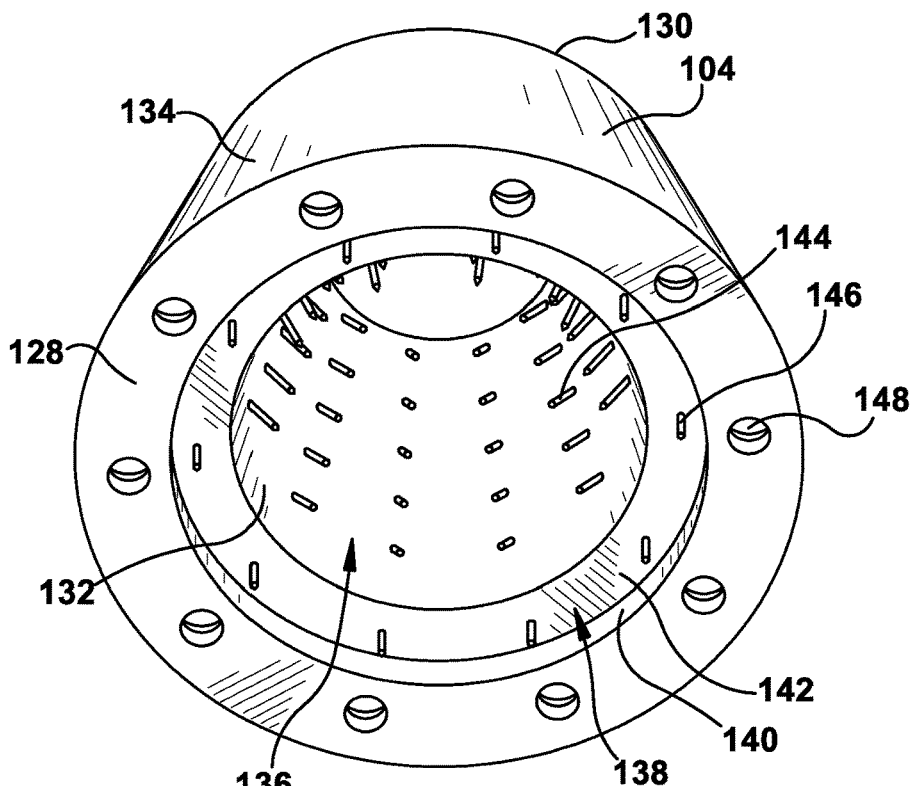
FIG. 2 is a perspective view of an element of aspect of FIG. 1.
Figure 3:
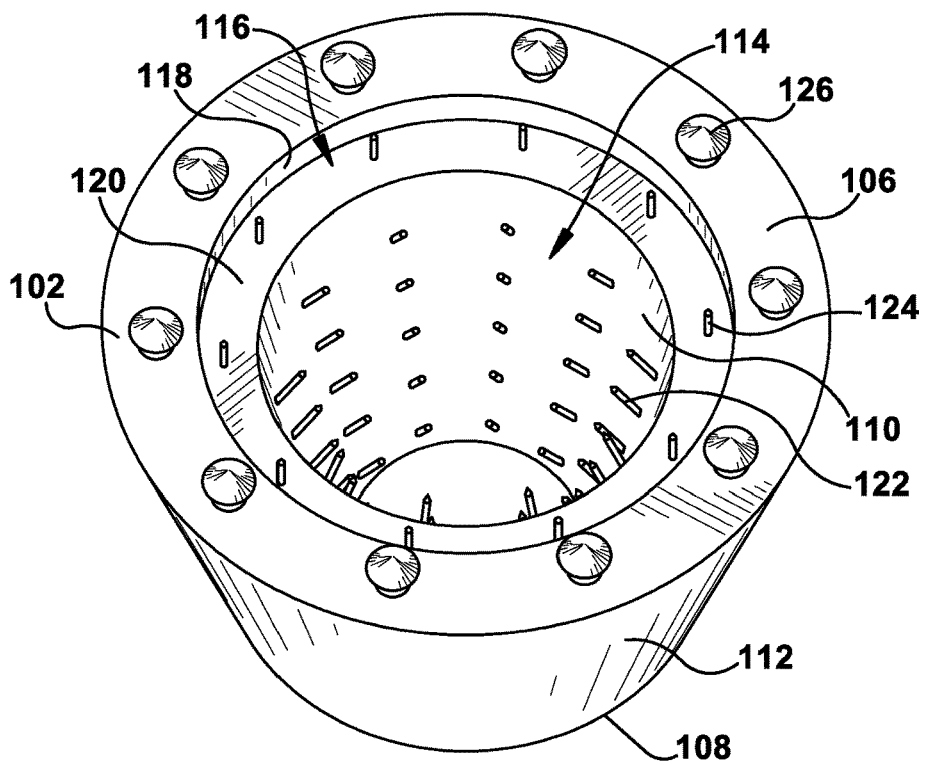
FIG. 3 is a perspective view of an element of the aspect of FIG. 1.

FIGS. 1-3 depict an example anastomotic coupler device 100 designed in accordance with the teachings of the present disclosure. The anastomotic coupler device 100 includes first and second rings 102, 104. The first ring 102 has a diameter that inwardly tapers from a first ring surface 106 to a second ring surface 108. The first and second ring surfaces 106, 108 face in longitudinally opposite directions. The term "longitudinal" is used herein to indicate a substantially vertical direction, in the orientation of FIG. 1, and is indicated at "LO" in FIG. 1. The inward taper of the first ring 102 shapes the first ring 102 as a funnel, flute, or truncated cone. Inner and outer surfaces 110, 112 of the first ring 102 longitudinally extend from the first ring surface 106 toward the second ring surface 108. The first ring 102 has an inner lumen 114 that is defined by the inner surface 110. As shown in FIG. 1, corresponding to the shape of the first ring 102, the inner lumen 114 may be substantially shaped as a funnel, flute, or truncated cone.

The first ring 102 has an annular central recession 116 between the inner surface 110 and the first ring surface 106. The central recession 116 is defined by a recession sidewall 118 that substantially longitudinally extends from the first ring surface 106, and a recession floor 120 that substantially laterally extends from the inner surface 110. The term "lateral" is used herein to indicate a direction substantially perpendicular to the "longitudinal" direction, is shown as the horizontal direction in the orientation of FIG. 1, and is indicated at "LA" in FIG. 1.

As shown in FIGS. 1-3, a plurality of spikes 122, 124 extend away from (e.g., directly from) at least one of the inner surface 110 and recession floor 120 of the first ring 102. For example, a first set of spikes 122 may extend at a desired angle, such as, but not limited to, about a 1-90 degree angle, and preferably about a 45-60 degree angle, with respect to the inner surface 110 away from the inner surface 110 into the inner lumen 114. A second set of spikes 124 may extend substantially perpendicularly away from (e.g., directly from) the recession floor 120. The second set of spikes 124 thus extend in the longitudinal direction. The first ring 102 may also include a plurality of posts 126 that extend substantially perpendicularly and longitudinally away from (e.g., directly from) the first ring surface 106.

The second ring 104 substantially mirrors the first ring 102. Thus, the second ring 104 includes oppositely facing first and second ring surfaces 128, 130, inner and outer surfaces 132, 134 longitudinally extending from the first ring surface 128 toward the second ring surface 130, an inner lumen 136, and a central recession 138 defined by a recession sidewall 140 and a recession floor 142. The second ring 104, and correspondingly the inner lumen 136 of the second ring 104, is also shaped as a funnel, flute, or truncated cone. The second ring 102 includes a first set of spikes 144 that may extend at a desired angle, such as, but not limited to, about a 1-90 degree angle, and preferably about a 45-60 degree angle, with respect to the inner surface 132 away from (e.g., directly from) the inner surface 132 into the inner lumen 136. The second ring 104 also includes a second set of spikes 146 that may extend substantially perpendicularly away from (e.g., directly from) the recession floor 142. However, unlike the first ring 102, the first ring surface 128 of the second ring 104 includes a plurality of receiver depressions 148 configured to receive the plurality of posts 126 when the first and second rings 102, 104 are joined together.

As shown in FIG. 1, in use, the first ring 102 is positioned over a first vessel end 150 of a cut vessel 152 so that the first vessel end 150 engages the inner surface 110. The vessel can be any fluid carrying tube, such as, but not limited to, an artery, a vein, an arteriole, a capillary, a venule, a bronchus, a bronchiole, and an intestine. The vessel 152 shown in FIG. 1 is an artery, for example. The first set of spikes 122 penetrate into a vessel wall 154 when the first vessel end 150 engages the inner surface 110 to hold the first vessel end 150 engaged to the first ring 102. An instrument 1080, such as a rubber micro-plunger 1080 (see FIG. 10), can be used to gently urge the first set of spikes 122 to penetrate into the vessel wall 154. Because of their angular extension, the first set of spikes 122 may penetrate the outer layer (the adventitia) 156 and the middle layer (the media) 158 of the vessel wall 154 without penetrating the inner most layer (the intima) 160. Alternatively, the first set of spikes 122 may penetrate the outer layer 156 of the vessel wall 154 without penetrating the middle and inner most layers 158, 160. In either case, the first set of spikes 122 penetrate the vessel wall 154 without disrupting the inner lining of the vessel 152.

An edge 162 of the first vessel end 150 is then everted onto the central recession 116 of the first ring 102. The second set of spikes 124 penetrate into the vessel wall 154 as the edge 162 of the first vessel end 150 is everted onto the central recession 116 to secure the first ring 102 to the edge 162 of the first vessel end 150. The micro-plunger 1080 can be used to gently urge the second set of spikes 124 to penetrate into the vessel wall 154. Similar, to the first set of spikes 122, the second set of spikes 124 can be configured so that they penetrate the vessel wall 154 without disrupting the inner lining of the vessel 152.

Before or after the first ring 102 is secured to the first vessel end 150, the second ring 104 is secured to a second vessel end 164 of the cut vessel 152 in a similar manner as described above. With the first and second rings 102, 104 secured to their respective vessel ends 150, 164, the first and second rings 102, 104 are joined together so that the first surfaces 106, 128 of the first and second rings 102, 104 abut (e.g., directly contact or directly engage) one another. The everted portions 162, 166 of the first and second vessel ends 150, 164 contact one another when the first and second rings 102, 104 are joined together. This end-to-end contact of the first and second vessel ends 150, 164 may lead to a successful anastomosis and help prevent the development of thrombosis.

It should be appreciated that, unlike known vein coupler devices, the first and second rings 102, 104 of the anastomotic coupler device 100 have inner surfaces 110, 132 that are inwardly tapered. The inward tapers of the inner surfaces 110, 132 combined with the angular extensions of the first set of spikes 122, 144 with respect to the inwardly tapered inner surfaces 110, 132 helps orient the first set of spikes 122, 144 into a desirable position for penetrating the first and second vessel ends 150, 164. Therefore, the inward tapers of the inner surfaces 110, 132 combined with the angular extensions of the first set of spikes 122, 144 with respect to the inwardly tapered inner surfaces 110, 132 help prevent the first and second vessel ends 150, 164 from undesirably egressing the first and second rings 102, 104.

Figure 4:
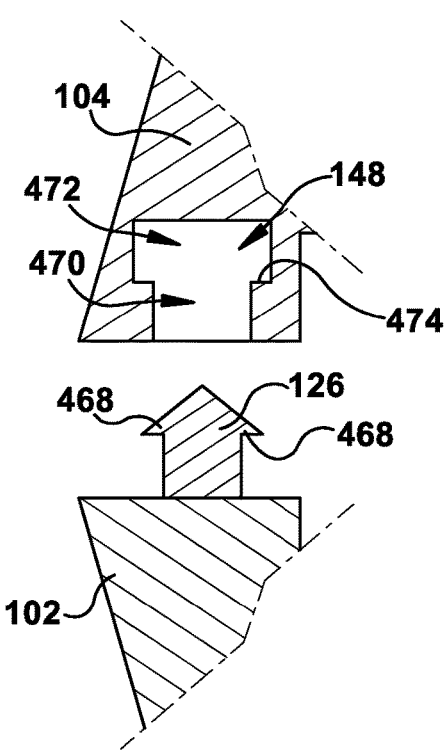
FIG. 4 is a cross-sectional view of an example configuration of an element of the aspect of FIG. 1.

The posts 126 of the first ring 102 are received in the receiver depressions 148 of the second ring 104 as the first and second rings 102, 104 are joined together. The anastomotic coupler device 100 may be configured so that the posts 126 do not penetrate the vessel wall 154 during use. The post-depression engagement helps to secure the first and second rings 102, 104 together. At least one of the posts 126 and/or the receiver depressions 148 may have locking features (e.g., barbs) to help prevent the posts 126 from undesirably egressing from the receiver depressions 148. For example, as shown in FIG. 4, at least one of the posts 126 can be substantially arrow-shaped and have at least one laterally extending projection 468. The projection 468 and/or the post 126 may be formed from an elastic material so that the projection 468 may at least partially flex as desired. An associated receiver depression 148 may have a first portion 470 that has a lateral width that is less than a lateral width of a second portion 472.

The post 126 may be configured so that the projection 468 flexes as the post 126 is inserted into the receiver depression 148 to permit the post 126 to pass through the first portion 470 of the receiver depression 148. Once the post 126 is fully inserted into the receiver depression 148, the projection 468 is positioned in the second portion 472 and snaps back to the projection's 468 pre-flexed condition. Engagement between the projection 468 and an abutting surface 474 of the second portion 472 at least partially prevents the post 126 from undesirably egressing the receiver depression 148. However, if a user desires to remove the post 126 from the receiver depression 148, the user can apply a predetermined force that is configured to cause the projection 468 to flex and permit the post 126 to pass through the first portion 470 of the receiver depression 140.

Alternatively, or in addition to the above, the locking features of the posts 126 and the receiver depressions 148 that at least partially prevent the posts 126 from egressing the receiver depressions 148 may comprise configuring the size and/or shape of the posts 128 and receiver depressions 148 to provide for a frictional or interference fit between the posts 126 and the receiver depressions 148. As another alternative or addition, the locking features may comprise configuring the posts 126 and the receiver depressions 148 to have at least one of magnets and ferromagnetic materials to provide for a magnetic engagement between the posts 126 and the receiver depressions 148.

The engagement between the posts 126 and the receiver depressions 148 also helps prevent one of the first and second vessel ends 150, 164 from laterally rotating relative to the other of the first and second vessel ends 150, 164 once the first and second rings 102, 104 are secured together. If the anastomosed first and second vessel ends 150, 164 were to rotate relative to one another, at least one of the first vessel end 150, the second vessel end 164, and the vessel 152 as a whole could become cinched or kinked, which may cause a delayed vessel thrombosis. The engagement between the posts 126 and the receiver depressions 148, however, prevents one of the first and second rings 102, 104 from laterally rotating relative to the other of the first and second rings 102, 104, which correspondingly helps prevent one of the first and second vessel ends 150, 164 from laterally rotating relative to the other of the first and second vessel ends 150, 164. Therefore, a user can laterally rotate each of the first and second vessels ends 150, 164 to a desired orientation, and then anastomose the first and second vessel ends 150, 164 by inserting the posts 126 into the receiver depressions 148 to prevent the first and second vessel ends 150, 164 from laterally rotating relative to one another.

Figure 5:
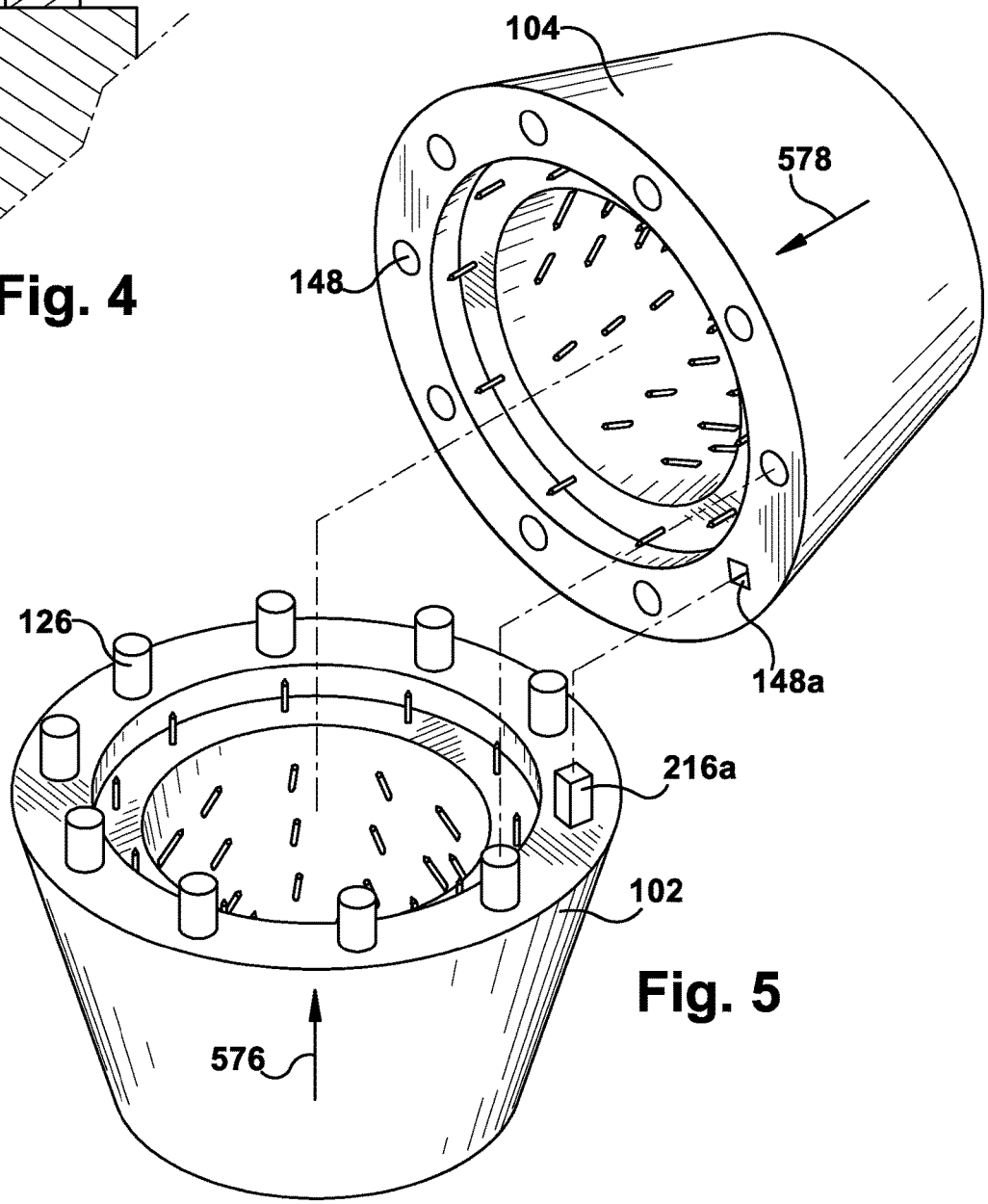
FIG. 5 is a perspective view of an example configuration of an element of the aspect of FIG. 1.
Figure 6:
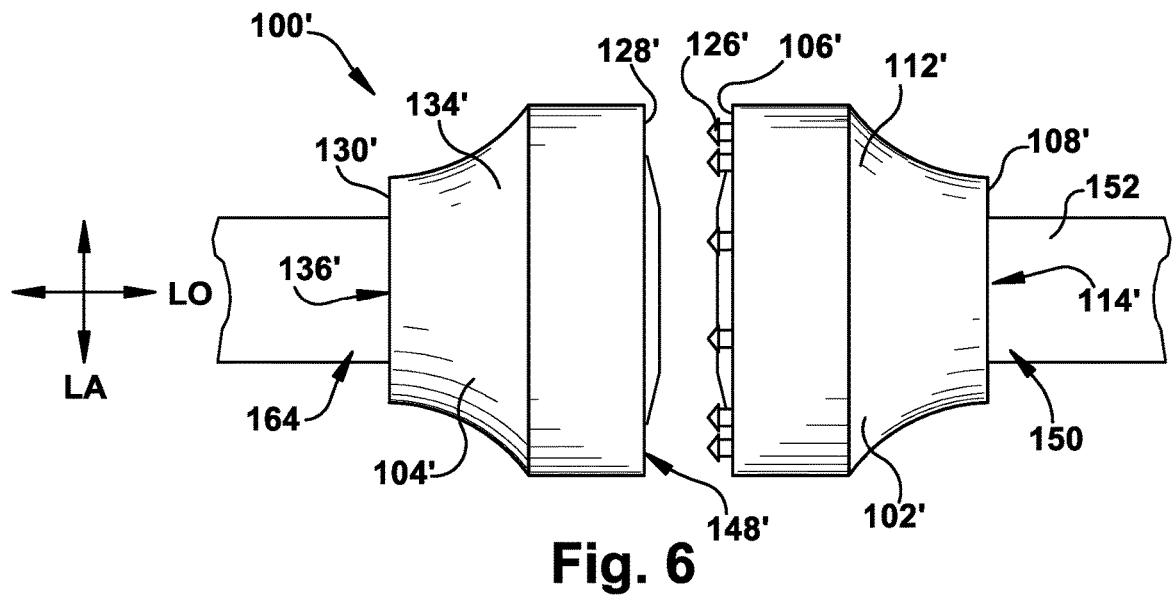
FIG. 6 is a side view of an anastomotic coupler device according to an aspect of the present invention, including the device in an example use environment.
Figure 7:
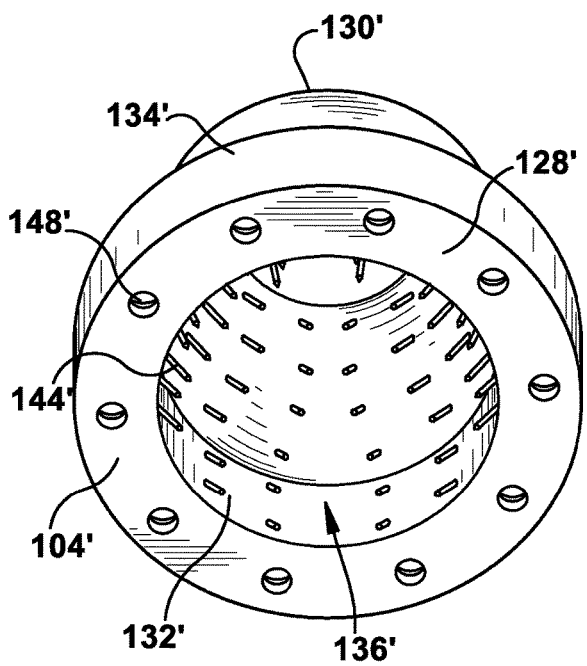
FIG. 7 is a perspective view of an element of the aspect of FIG. 6.
Figure 8:
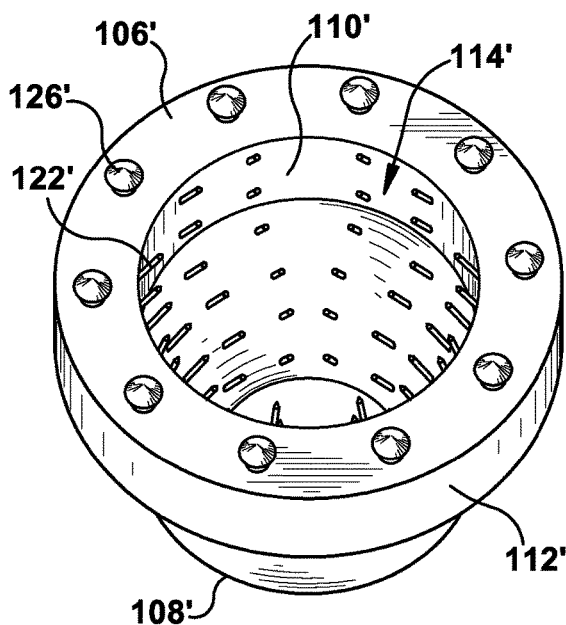
FIG. 8 is a perspective view of an element of the aspect of FIG. 6.

At least one of the first and second rings 102, 104 may have orientation features configured to confirm that the first and second rings 102, 104 are desirably orientated relative to one another. For example, as shown in FIG. 5, at least one of the posts 126 can be configured to be received in only one correspondingly configured receiver depression 148. In the example configuration of FIG. 5, one of the posts 126 (shown here as post 126a) is substantially shaped as a square prism, while the other posts 126 are substantially shaped as cylinders. Similarly, one of the receiver depressions 148 (shown here as receiver depression 148a) is substantially square-shaped, while the other receiver depressions 148 are substantially circular. The post 126a can only be inserted into the square-shaped receiver depression 148a. Therefore, the first and second rings 102, 104 may be brought into abutting engagement with one another only if the post 126a is aligned with the receiver depression 148a. This configuration helps confirm that the first and second rings 102, 104 are oriented as desired before being attached to one another.

Further, as shown in the example configuration of FIG. 5, each of the first and second rings 102, 104 can have orientation indicators 576, 578 on or recessed into the outer surfaces 112, 134 of the first and second rings 102, 104. The first and second rings 102, 104 may be configured such that the orientation indicators 576, 578 align with one another only when the first and second rings 102, 104 are oriented as desired relative to one another.

FIGS. 6-9 depict another example anastomotic coupler device 100' designed in accordance with the teachings of the present disclosure. The anastomotic coupler device 100' of FIGS. 4-7 is similar to the to the anastomotic coupler device 100 of FIGS. 1-3 and therefore, structures that are the same as or similar to those described with reference to FIGS. 1-3 have the same reference numbers with the addition of a "prime" mark. Description of common elements and operation similar to those in the previously described the anastomotic coupler device 100 of FIGS. 1-3 may not be repeated with respect to the anastomotic coupler device 100' of FIGS. 6-9, but should instead be considered to be incorporated below by reference as appropriate. Furthermore, elements shown or described with respect to one of the example anastomotic coupler devices 100, 100' may be shared by the other of the example anastomotic coupler devices 100, 100' whether expressly stated, shown, or not.

The anastomotic coupler device 100' of FIGS. 6-9 is similar to the anastomotic coupler device 100 of FIGS. 1-3, except that the anastomotic coupler device 100' of FIGS. 6-9 does not include central recessions 116 on the first and second rings 102', 104'. Therefore, the first and second rings 102', 104' of the anastomotic coupler device 100' do not include the second set of spikes 124. However, it is contemplated that the first and second rings 102', 104' of the anastomotic coupler device 100' may be configured to include the central recessions 116 and the second set of spikes 124.

Figure 9:
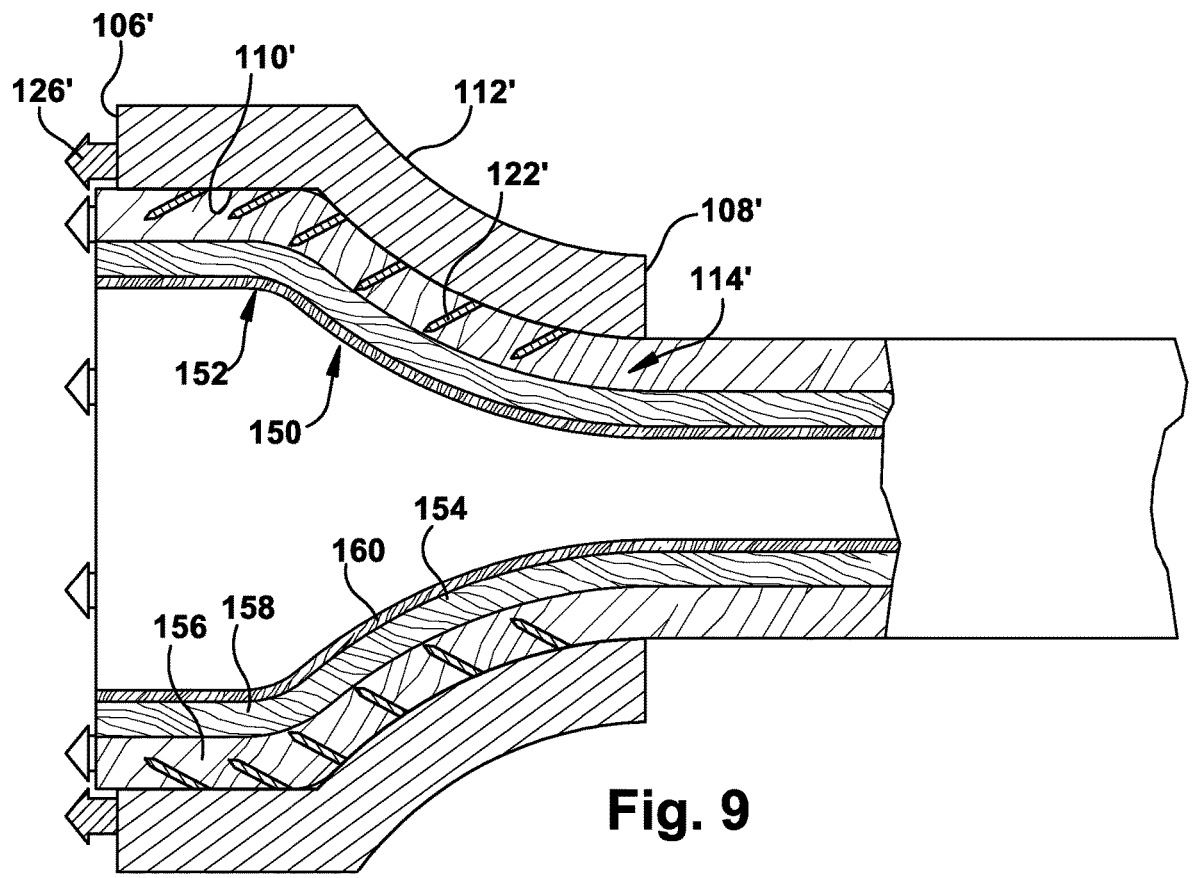
FIG. 9 is a cross-sectional view of a portion of the aspect of FIG. 6, including the device in an example use environment.

The anastomotic coupler device 100' also differs from the anastomotic coupler device 100 in that the first and second rings 102', 104' are shaped as a semi-octagon or trapezoid instead of a funnel, flute, or truncated cone. Therefore, as shown in FIG. 9, the inner lumen 114' of the first ring 102' corresponds to the shape of the first ring 102' and is semi-octagonal or trapezoidal. Although not shown, the inner lumen 136' of the second ring is also semi-octagonal or trapezoidal.

Figure 10:
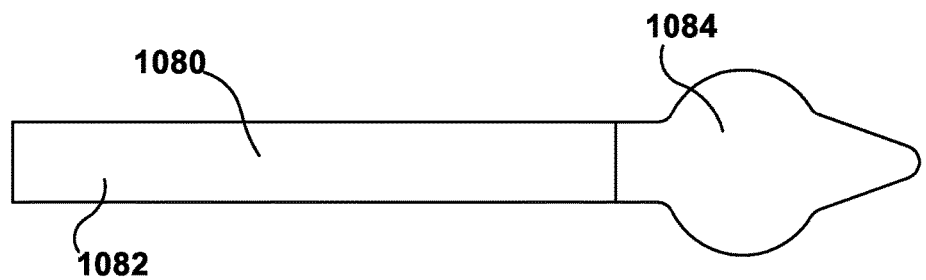
FIG. 10 is a side view of an element that may be used in conjunction with the device.

The anastomotic coupler device 100' may be used in an anastomosis procedure in a similar manner as described above. Therefore, the description of use above will not be repeated, for brevity, but is incorporated by reference, mutatis mutandis. As described above, during an anastomosis procedure, an instrument 1080, such as a rubber microplunger 1080, can be utilized to gently ensure that the spikes 122, 122', 144, 144', 124, 124', 146, 146' penetrate into the vessel wall 154. FIG. 10 depicts an example rubber microplunger 1080 that includes a handle portion 1082 and a rubber tip portion 1084.

The first set of spikes 122, 122', 144, 144', the second set of spikes 124, 124', 146, 146', and/or the posts 126, 126' can each be made out of the same materials as the first and second rings 102, 102', 104, 104'. In such a configuration, the first set of spikes 122, 122', 144, 144', the second set of spikes 124, 124', 146, 146', and/or the posts 126, 126' can each can be integrally or monolithically formed as one-piece with the first and second rings 102, 102', 104, 104', or separately formed from and joined to the first and second rings 102, 102', 104, 104'. Alternatively, the first set of spikes 122, 122', 144, 144', the second set of spikes 124, 124', 146, 146', and/or the posts 126, 126' can each be made out of materials different from those used to form the first and second rings 102, 102', 104, 104'. In such a configuration, the first set of spikes 122, 122', 144, 144', the second set of spikes 124, 124', 146, 146', and/or the posts 126, 126' can each be separately formed from and joined to the first and second rings 102, 102', 104, 104'. The first set of spikes 122, 122', 144, 144', the second set of spikes 124, 124', 146, 146', and/or the posts 126, 126' can each be separately formed from and joined to the first and second rings 102, 102', 104, 104' by being bonded, sealed, adhered, press-fit, insert molded, overmolded, by any other suitable direct or indirect attachment or coupling means, or by any combination thereof.

Figure 11:
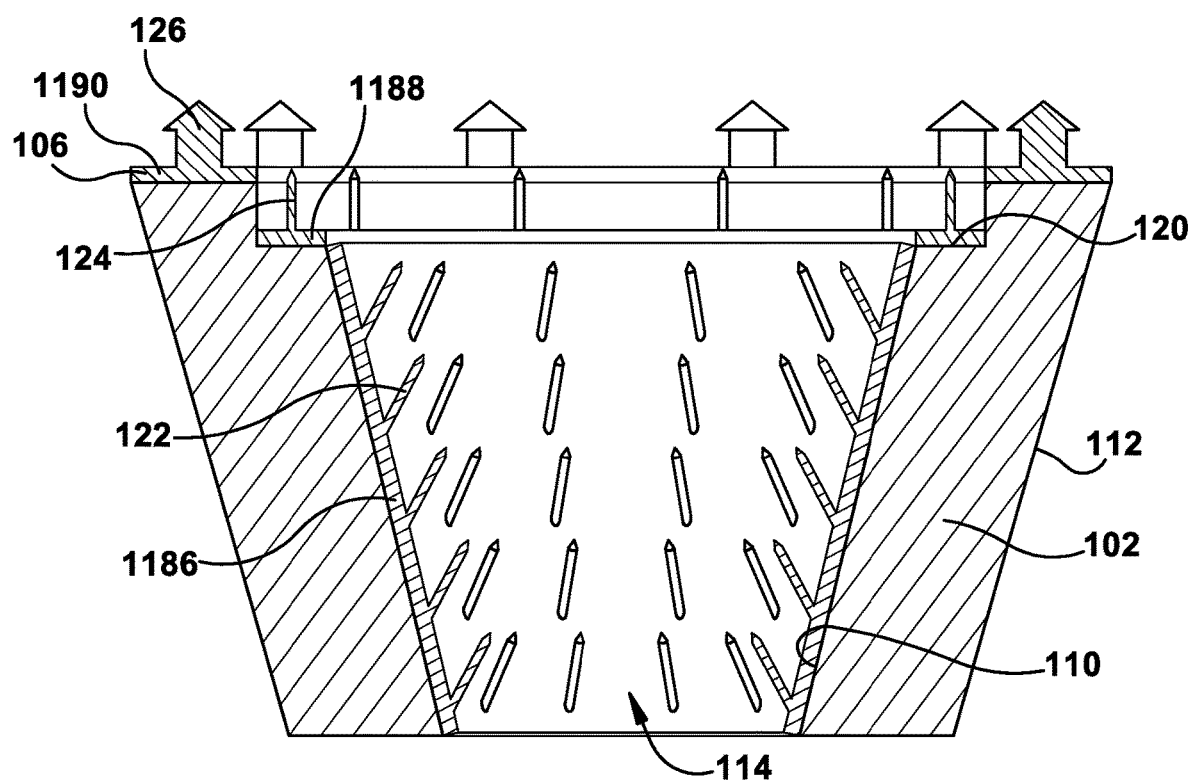
FIG. 11 is a cross-sectional view of an example configuration of an element of the aspect of FIG. 1.

FIG. 11 depicts an example configuration in which the first set of spikes 122, the second set of spikes 124, and the posts 126 can each be separately formed from and then joined to the first ring 102. Although the second ring 104 is not shown in FIG. 11, portions of the below description may also apply for joining the first and second set of spikes 144, 146 to the second ring 104. As shown in FIG. 11, the first set of spikes 122 may be provided on a first layer of material 1186. The first set of spikes 122 may be formed integrally as one piece with the first layer of material 1186, or separately from and then joined to the first layer of material 1186. With the first set of spikes 122 on the first layer of material 1186, the first layer of material 1186 can be joined to the inner surface 110 of the first ring 102. In this configuration, the first layer of material 1186 may help define the inner lumen 114, and may contact the vessel wall 154 when in use.

The second set of spikes 124 may be provided on a second layer of material 1188. The second set of spikes 124 may be formed integrally as one piece with the second layer of material 1188, or separately from and then joined to the second layer of material 1188. With the second set of spikes 124 on the second layer of material 1188, the second layer of material 1188 can be joined to the recession floor 120 of the first ring 102. In this configuration, the second layer of material 1188 may help define the inner lumen 114, and may contact the vessel wall 154 when in use. Because the recession floor 120 may be annular, the second layer of material 1188 may be ring-shaped for interfacing with the annular recession floor 120.

The posts 126 may be provided on a third layer of material 1190. The posts 126 may be formed integrally as one piece with the third layer of material 1190, or separately from and then joined to the third layer of material 1190. With the posts 126 on the third layer of material 1190, the third layer of material 1190 can be joined to the first ring surface 106 of the first ring 102. Because the first ring surface 106 of the first ring 102 may be annular, the third layer of material 1190 may be ring-shaped for interfacing with the annular first ring surface 106.

The first ring 102, 102', the second ring 104, 104', the first set of spikes 122, 122', 144, 144', the second set of spikes 124, 124', 146, 146', the posts 126', 126', the instrument 1080, the first layer of material 1186, the second layer of material 1188, and/or the third layer of material 1190 can each be at least partially formed from silicone, rubber, polyvinyl chloride, polyethylene, polypropylene, nylon, stainless steel, titanium, any other metal, any other biocompatible material, or any combination thereof.

Figure 12:
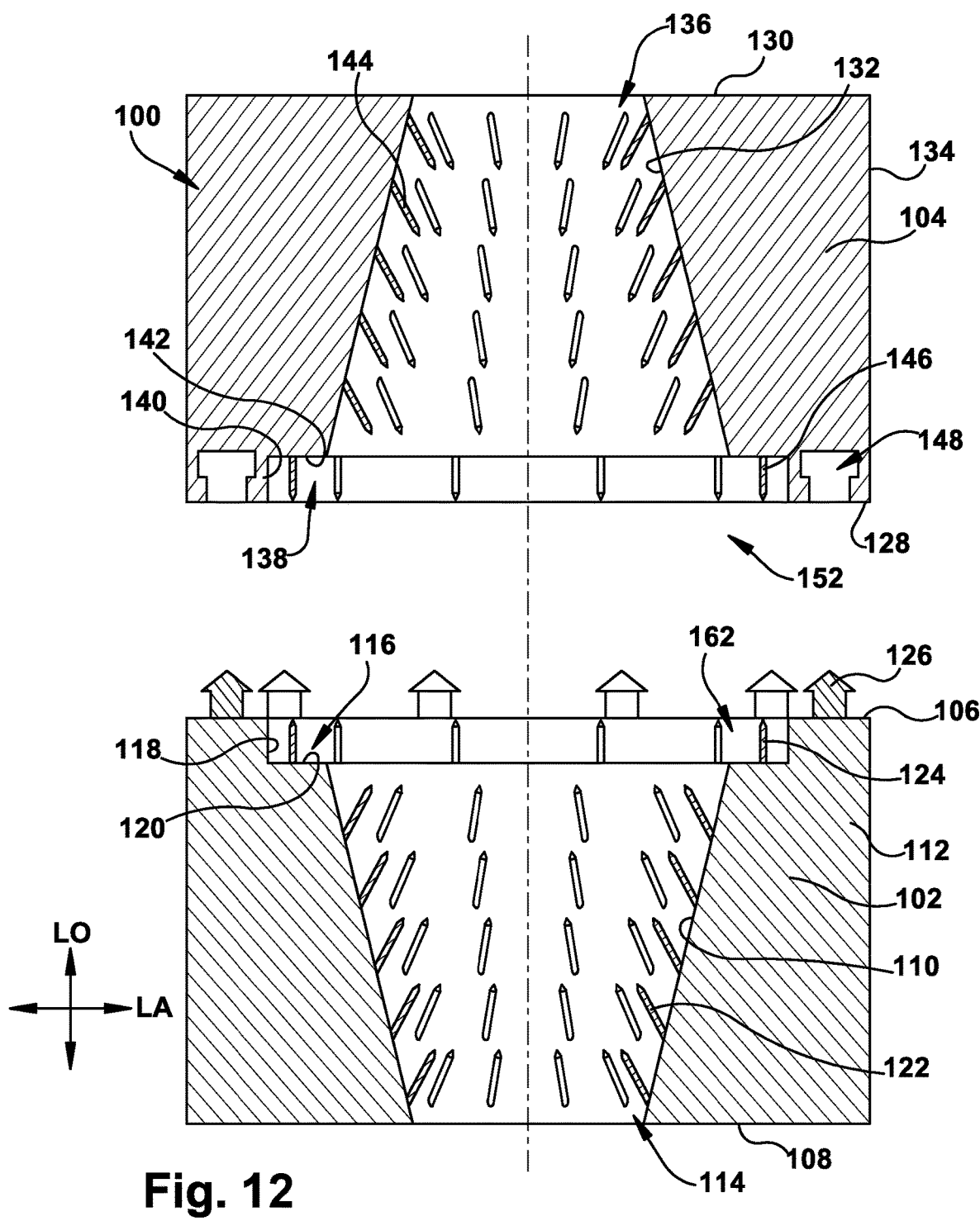
FIG. 12 is a cross-sectional view of an example configuration of an element of the aspect of FIG. 1.
Figure 13:
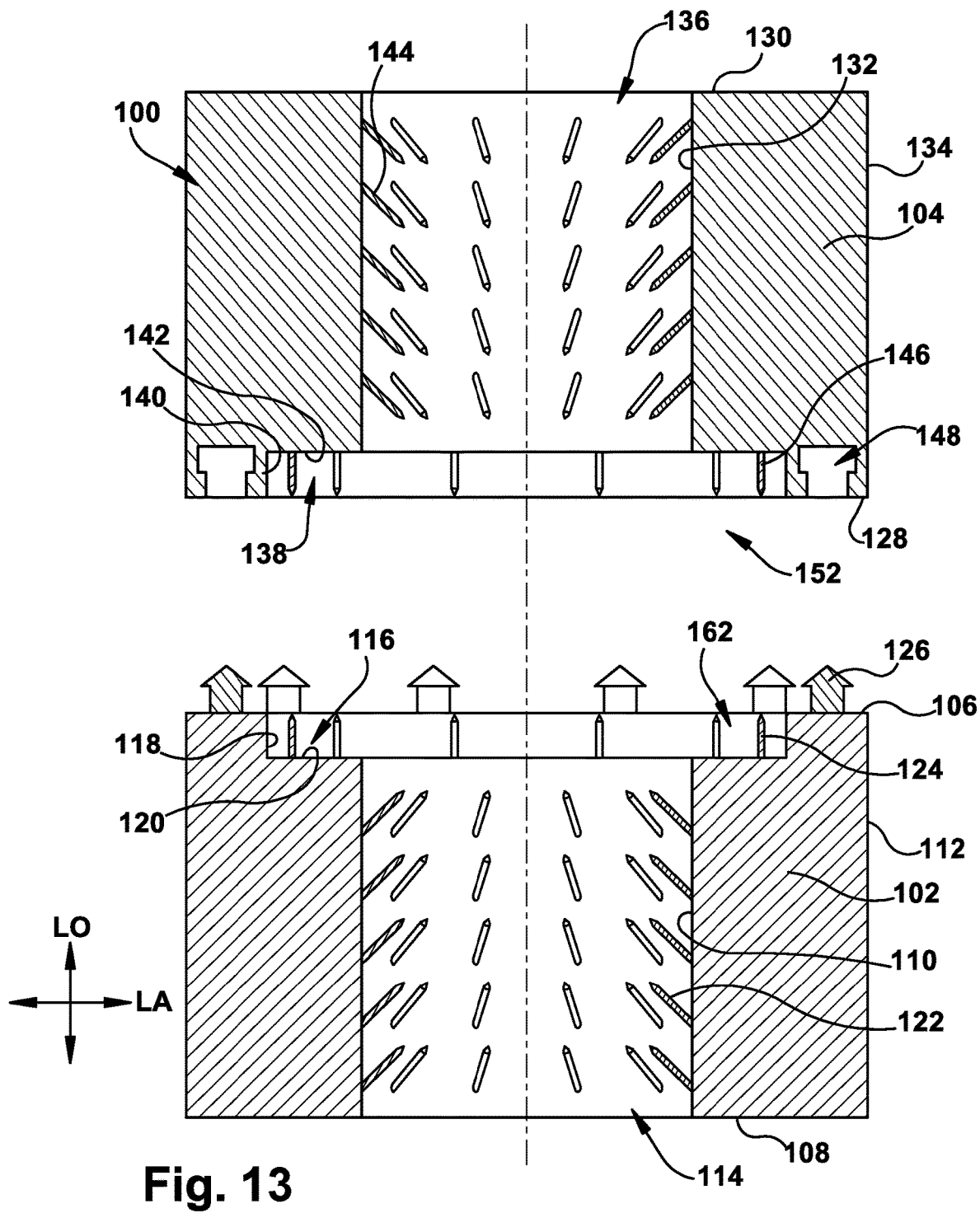
FIG. 13 is a cross-sectional view of an example configuration of an element of the aspect of FIG. 1.

Although the rings 102, 104 have been described as being shaped as a funnel, flute, truncated cone, or semi-octagon, the rings 102, 104 may have any desirable shape. For example, as shown in FIG. 12, the outer surfaces 112, 134 of the rings 102, 104 may be shaped as cylinders so that the outer diameters of the rings 102, 104 do not substantially inwardly or outwardly taper from the first ring surfaces 106, 128 to the second ring surfaces 108, 130, while the inner diameters defined by the inner surfaces 110, 132 of the rings 102, 104 inwardly taper from the first ring surfaces 106, 128 to the second ring surfaces 108, 130. The inner lumens 114, 136 of the rings 102, 104 of FIG. 12 thus inwardly taper from the first ring surfaces 106, 128 to the second ring surfaces 108, 130. Alternatively, as shown in FIG. 13, the first and second rings 102, 104 may be shaped as rings or cylinders with continuous outer and inner diameters (i.e., diameters that do not substantially inwardly or outwardly taper from the first ring surfaces 106, 128 to the second ring surfaces 108, 130). The inner lumens 114, 136 of the rings 102, 104 of FIG. 13 thus are substantially shaped as cylinders.

In summary, and stated differently, the present invention is described as having aspects which may include:
(1) rings that are shaped as, for example, a funnel, flute, truncated cone, semi-octagon, or cylinder,
(2) spikes, which may be at about a 45-60 degree angle with respect to the inner lumen of a ring, to hold the vessel end of a cut vessel by penetrating into the outer layer of the vessel wall without interrupting the innermost layer of the vessel wall,
(3) an annular central recession between an inner surface and a first ring surface of a ring on which a portion of a vessel end can be everted,
(4) a plurality of spikes that extend substantially perpendicularly and longitudinally from a recession floor of a central recession for penetrating and holding an everted portion of a vessel end, and
(5) posts on a first ring that are received in receiver depression on a second ring to secure the first and second rings together and prevent lateral rotation of the first and second rings with respect to one another.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many use applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

We claim:

1. An apparatus for anastomosing a cut vessel, the apparatus comprising:
    a first ring having longitudinally spaced first and second ring surfaces and an inner surface longitudinally extending between the first and second ring surfaces, the inner surface of the first ring defining an inner lumen configured to receive a first vessel end of the cut vessel, the first ring including an annular central recession between the inner surface and the first ring surface, the annular recession of the first ring being defined by a longitudinally extending recession sidewall and a laterally extending recession floor, the inner surface of the first ring having at least one inner surface spike extending away from the inner surface into the inner lumen, the at least one inner surface spike of the first ring being configured to penetrate a vessel wall of the first vessel end and secure the first ring to the first vessel end, the recession floor of the first ring including at least one floor spike longitudinally extending therefrom for penetrating an everted portion of the first vessel end; and
    a second ring having longitudinally spaced first and second ring surfaces and an inner surface longitudinally extending between the first and second ring surfaces, the inner surface of the second ring defining an inner lumen configured to receive a second vessel end of the cut vessel, the second ring including an annular central recession between the inner surface and the first ring surface, the annular recession of the second ring being defined by a longitudinally extending recession sidewall and a laterally extending recession floor, the inner surface of the second ring having at least one inner surface spike extending away from the inner surface into the inner lumen, the at least one inner surface spike of the second ring being configured to penetrate a vessel wall of the second vessel end and secure the second ring to the second vessel end, the recession floor of the second ring including at least one floor spike longitudinally extending therefrom for penetrating an everted portion of the first vessel end;
    wherein the first and second rings, after being secured to the first and second vessel ends, are configured to be joined together into direct engagement to anastomose the cut vessel.

2. The apparatus of claim 1, wherein the at least one inner surface spike of the first ring extends at about a forty-five (45) to about a sixty (60) degree angle with respect to the inner surface of the first ring, and the at least one inner surface spike of the second ring extends at about a forty-five (45) to about a sixty (60) degree angle with respect to the inner surface of the second ring.

3. The apparatus of claim 1, wherein the first ring surface of the first ring includes at least one post configured to be received in a corresponding receiver depression on the first ring surface of the second ring when the first and second rings are joined together.

4. The apparatus of claim 3, wherein a portion of the at least one post is configured to engage a portion of the corresponding receiver depression to at least partially prevent the at least one post from egressing the corresponding receiver depression.

5. The apparatus of claim 3, wherein the first and second ring are at least partially prevented from rotating relative to one another when the at least one post is received in the corresponding receiver depression.

6. The apparatus of claim 1, wherein
    the first ring includes and an outer surface longitudinally extending between the first and second ring surfaces, the outer surface of the first ring having an orientation indicator, and
    the second ring includes and an outer surface longitudinally extending between the first and second ring surfaces, the outer surface of the second ring having an orientation indicator, the orientation indicators of the first and second rings being configured to align with one another when the first and second rings are joined together.

7. The apparatus of claim 1, wherein
    the first ring has a first layer of material that is separately formed from the first ring and joined to the inner surface of the first ring, the at least one inner surface spike of the first ring being provided on the first layer of material, the first ring having a second layer of material that is separately formed from the first ring and joined to the recession floor of the first ring, the at least one floor spike of the first ring being provided on the second layer of material, and
    the second ring has a first layer of material that is separately formed from the second ring and joined to the inner surface of the second ring, the at least one inner surface spike of the second ring being provided on the first layer of material, the second ring having a second layer of material that is separately formed from the second ring and joined to the recession floor of the second ring, the at least one floor spike of the second ring being provided on the second layer of material.

8. The apparatus of claim 1, wherein each of the first and second rings are shaped as a funnel, flute, truncated cone, or semi-octagon.

9. The apparatus of claim 1, wherein
    the inner lumen of the first ring inwardly tapers from the first ring surface to the second ring surface of the first ring, and
    the inner lumen of the second ring inwardly tapers from the first ring surface to the second ring surface of the second ring.

10. A method anastomosing a cut vessel, the method comprising:
    providing the apparatus of claim 1;
    positioning the first ring over a first vessel end of the cut vessel so that the first vessel end is in the inner lumen and surrounded by the inner surface of the first ring;
    penetrating a vessel wall of the first vessel end with the at least one inner surface spike of the first ring to secure the first ring to the first vessel end;
    positioning the second ring over a second vessel end of the cut vessel so that the second vessel end is in the inner lumen and surrounded by the inner surface of the second ring;
    penetrating a vessel wall of the second vessel end with the at least one inner surface spike of the second ring to secure the second ring to the second vessel end; and with the first and second rings secured to the first and second vessel ends, joining the first and second rings together to anastomose the cut vessel.

11. The method of claim 10, further comprising:
everting an edge of the first vessel end onto the central recession of the first ring;
penetrating the vessel wall of the first vessel end with the at least one floor spike of the first ring to secure the first ring to the edge of the first vessel end;
everting an edge of the second vessel end onto the central recession of the second ring; and
penetrating the vessel wall of the second vessel end with the at least one floor spike of the second ring to secure the second ring to the edge of the second vessel end.

12. An apparatus for anastomosing a cut vessel, the apparatus comprising:
a first ring having longitudinally spaced first and second ring surfaces and an inner surface longitudinally extending between the first and second ring surfaces, the inner surface defining an inner lumen configured to receive a first vessel end of the cut vessel, the inner surface having at least one spike extending away from the inner surface into the inner lumen, the at least one spike of the first ring being configured to penetrate a vessel wall of the first vessel end and secure the first ring to the first vessel end; and
a second ring having longitudinally spaced first and second ring surfaces and an inner surface longitudinally extending between the first and second ring surfaces, the inner surface defining an inner lumen configured to receive a second vessel end of the cut vessel, the inner surface having at least one spike extending away from the inner surface into the inner lumen, the at least one spike of the second ring being configured to penetrate a vessel wall of the second vessel end and secure the second ring to the second vessel end;
wherein the first and second rings, after being secured to the first and second vessel ends, are configured to be joined together into direct engagement to anastomose the cut vessel; and
wherein the first ring surface of the first ring includes a plurality of posts and the first ring surface of the second ring includes a plurality of receiver depressions that receive the plurality of posts when the first and second rings are joined together, at least one of the posts being configured to be received in only one correspondingly configured receiver depression.

13. The apparatus of claim 12, wherein the at least one spike of the first ring extends at about a forty-five (45) to about a sixty (60) degree angle with respect to the inner surface of the first ring, and the at least one spike of the second ring extends at about a forty-five (45) to about a sixty (60) degree angle with respect to the inner surface of the second ring.

14. The apparatus of claim 12, wherein a portion of at least one of the posts is configured to engage a portion of a corresponding receiver depression to at least partially prevent the at least one post from egressing the corresponding receiver depression.

15. The apparatus of claim 12, wherein the first and second ring are at least partially prevented from rotating relative to one another when the posts are received in the receiver depressions.

16. The apparatus of claim 12, wherein
the first ring includes and an outer surface longitudinally extending between the first and second ring surfaces, the outer surface of the first ring having an orientation indicator, and
the second ring includes and an outer surface longitudinally extending between the first and second ring surfaces, the outer surface of the second ring having an orientation indicator, the orientation indicators of the first and second rings being configured to align with one another when the first and second rings are joined together.

17. The apparatus of claim 12, wherein
the first ring includes an annular central recession between the inner surface and the first ring surface, the annular recession being defined by a longitudinally extending recession sidewall and a laterally extending recession floor, the recession floor including at least one spike longitudinally extending therefrom for penetrating an everted portion of the first vessel end, and
the second ring includes an annular central recession between the inner surface and the first ring surface, the annular recession being defined by a longitudinally extending recession sidewall and a laterally extending recession floor, the recession floor including at least one spike longitudinally extending therefrom for penetrating an everted portion of the second vessel end.

18. The apparatus of claim 17, wherein
the first ring has a first layer of material that is separately formed from the first ring and joined to the inner surface of the first ring, the at least one spike that extends away from the inner surface of the first ring being provided on the first layer of material, the first ring having a second layer of material that is separately formed from the first ring and joined to the recession floor of the first ring, the at least one spike that extends away from the recession floor of the first ring being provided on the second layer of material, and
the second ring has a first layer of material that is separately formed from the second ring and joined to the inner surface of the second ring, the at least one spike that extends away from the inner surface of the second ring being provided on the first layer of material, the second ring having a second layer of material that is separately formed from the second ring and joined to the recession floor of the second ring, the at least one spike that extends away from the recession floor of the second ring being provided on the second layer of material.

19. The apparatus of claim 12, wherein each of the first and second rings are shaped as a funnel, flute, truncated cone, or semi-octagon.

20. The apparatus of claim 12, wherein
the inner lumen of the first ring inwardly tapers from the first ring surface to the second ring surface of the first ring, and
the inner lumen of the second ring inwardly tapers from the first ring surface to the second ring surface of the second ring.

21. A method anastomosing a cut vessel, the method comprising:
providing the apparatus of claim 12;
positioning the first ring over a first vessel end of the cut vessel so that the first vessel end is in the inner lumen and surrounded by the inner surface of the first ring;

penetrating a vessel wall of the first vessel end with the at least one spike that extends away from the inner surface of the first ring to secure the first ring to the first vessel end;

positioning the second ring over a second vessel end of the cut vessel so that the second vessel end is in the inner lumen and surrounded by the inner surface of the second ring;

penetrating a vessel wall of the second vessel end with the at least one spike that extends away from the inner surface of the second ring to secure the second ring to the second vessel end; and with the first and second rings secured to the first and second vessel ends, joining the first and second rings together to anastomose the cut vessel.

22. The method of claim 21, wherein the first ring includes an annular central recession between the inner surface and the first ring surface, the annular recession being defined by a longitudinally extending recession sidewall and a laterally extending recession floor, the recession floor including at least one spike longitudinally extending away from the recession floor, and the second ring includes an annular central recession between the inner surface and the first ring surface, the annular recession being defined by a longitudinally extending recession sidewall and a laterally extending recession floor, the recession floor including at least one spike longitudinally extending away from the recession floor, the method further comprising:

everting an edge of the first vessel end onto the central recession of the first ring;

penetrating the vessel wall of the first vessel end with the at least one spike that extends away from the recession floor of the first ring to secure the first ring to the edge of the first vessel end;

everting an edge of the second vessel end onto the central recession of the second ring; and penetrating the vessel wall of the second vessel end with the at least one spike that extends away from the recession floor of the second ring to secure the second ring to the edge of the second vessel end.

\* \* \* \* \*